United States Patent [19]

Backman et al.

[11] Patent Number: 4,753,883

[45] Date of Patent: Jun. 28, 1988

[54] ENZYME DEREGULATION

[75] Inventors: Keith C. Backman, Bedford; Ramaswamy Balakrishnan, Framingham, both of Mass.

[73] Assignee: Biotechnica International, Inc., Cambridge, Mass.

[21] Appl. No.: 860,541

[22] Filed: May 7, 1986

[51] Int. Cl.$^4$ .......................... C12N 9/88; C12N 9/90; C07K 13/00
[52] U.S. Cl. .................................... 435/232; 435/233; 435/317; 530/350
[58] Field of Search ................ 530/350; 435/317, 232, 435/233

[56] References Cited
FOREIGN PATENT DOCUMENTS 7272781 7/1981 Australia .

OTHER PUBLICATIONS

Hudson and Davidson, *J. Mol. Biol.* 180:1023–1051 (1984).
Baldwin et al. *Arch. Biochem. Biophys.* 211:66–85 (1981).
Gething and Davidson, *Eur. J. Biochem.* 86:159–164 (1978).
Gething and Davidson *Eur. J. Biochem.* 86:165–174 (1978).
Gething and Davidson *Eur. J. Biochem.* 78:111–117 (1977).

*Primary Examiner*—John Kight
*Assistant Examiner*—Christina Chan

[57] ABSTRACT

Proteins having chorismate mutase-prephenate dehydratase (CMPD) activity, but lacking phenylalanine sensitivity are produced by genetic engineering. The proteins contain a sequence substantially corresponding to the N-terminal 337 amino acids of *Escherichia coli* CMPD. Expression vectors including genes coding for those proteins and regulatory DNA enabling their expression are used to transform host microorganisms, which are cultured to produce phenylalanine.

7 Claims, 9 Drawing Sheets

ENZYME DEREGULATION

BACKGROUND OF THE INVENTION

This invention relates to enzymes having chorismate mutase and/or prephenate dehydratase activity, and their use in the production of desired compounds such as phenylalanine.

The phenylalanine synthesis pathway in microbes is known to include reactions catalyzed by a single dual-function enzyme, or two separate enzymes, having chorismate mutase and prephenate dehydratase (CMPD) activity. Generally, this activity is subject to feedback inhibition from phenylalanine. *Escherichia coli* have a chromosomal gene encoding CMPD activity, termed pheA.

Tribe, Australian Published Application No. 72727/81 discloses an *E. coli* mutant termed NST37 said to produce chorismate mutase prephenate dehydratase substantially free from inhibition by phenylalanine.

Hudson and Davidson, *J. Mol. Biol.* 180: 1023-1051 (1984), disclose the nucleotide sequence of *E. coli* pheA.

Baldwin et al., *Arch. Biochem. Biophys.* 211: 66-85 (1981), disclose that increasing phenylalanine concentration converts dimeric CMPD to inactive tetramers and octamers.

Gething and Davidson, *Eur. J. Biochem.* 86: 159-164 (1978), disclose that changes in the CMPD aggregation state do not induce gross secondary structural changes, and when CMPD is exposed to phenylalanine, a tryptophanyl residue moves into a more hydrophobic microenvironment.

Gething and Davidson, *Eur. J. Biochem.* 86: 165-174 (1978), disclose that modification of CMPD cysteinyl residues with 5,5-dithiobis[nitrobenzoate] desensitizes CMPD to phenylalanine feedback inhibition.

Gething and Davidson, *Eur. J. Biochem.* 78: 111-117 (1977), disclose that modification of the two tryptophanyl residues of CMPD, using dimethyl[2-hydroxy-5-nitrobenzyl sulphonium bromide], results in a partially active, feedback resistant enzyme.

SUMMARY OF THE INVENTION

We have discovered a class of proteins possessing CMPD activity that are substantially insensitive to phenylalanine feedback inhibition. The proteins have the formula:

where $\Gamma$ is an amino acid sequence having CMPD activity, substantially corresponding to the N-terminal 337 amino acid sequence of *E. coli* CMPD; CO is the carbonyl group of the C-terminal amino acid residue of $\Gamma$; and $\Delta$ is —OH, —O⁻, an amino acid residue other than tryptophan connected via a peptide bond to the C-terminal residue of $\Gamma$, or an amino acid sequence having an N-terminal residue other than tryptophan, connected via a peptide bond to the C-terminal residue of $\Gamma$.

"Substantially corresponding" to the CMPD sequence means having sufficient homology to retain activity substantially equivalent to CMPD. For example, sequences of pheA genes of bacteria related to *E. coli* having such homology are included. Minor alterations in structure (e.g., the addition, deletion, or nonconservative substitution of a limited number of residues or the conservative substitution of many residues) which retain substantial activity are included within the meaning of that term.

Preferably $\Gamma$ comprises amino acids 1-337 of *E. coli* CMPD. That sequence can be determined from pKB912 or pKB702, described below, or from the following sequence published by Hudson and Davidson (1984), cited above, where the single-letter codes refer to the table given below:

MTSENPLLALREKISALDEKLLALLAERRELAVEVGKAKL
LSHRPVRDIDRERDLLERLIJLGKAHHLDAHYITRLFQLI
IEDSVLTQQALLQQHLNKINPHSARIAFLGPKGSYSHLAA
RQYAARHFEQFIESGCAKFADIFNQVETGQADYAVVPIEN
TSSGAINDVYDLLQHTSLSIVGEMTLTIDHCLLVSGTTDL
STINTVYSHPQPFQQCSKFLNRYPHWKIEYTESTSAAMEK
VAQAKSPHVAALGSEAGGTLYGLQVLERIEANQRQNFTRF
VVLARKAINVSDQVPAKTTLLMATGQQAGALVEALLVLRN
HNLIMTRLESRPIHGNP.

Also preferably, $\Delta$ is —OH or —O⁻. Alternatively, $\Delta$ is the amino acid sequence $\Psi$-$\Omega$ where: $\Psi$ is either an amino acid residue other than tryptophan or an amino acid sequence whose N-terminal residue is a residue other than tryptophan; and $\Omega$ is the sequence EEMFYLDIQANLESAEMQKALKELGITRSMKVL-GCYPSENVVPVDPT, or a sequence coding for enzymatic activity other than CMPD activity, preferably the activity of a phenylalanine synthesis pathway enzyme. Another activity-encoding sequence suitable for $\Omega$ is the lacZ$\alpha$, which can be derived from the portion of pUC19 encoding lacZ$\alpha$, Yanisch-Perron et al. (1985) *Gene* 33: 103, or it can be the following sequence RRIPGNSLAVVLQRRDWENPGVTQLN-RLAAHPPFASWRNSEEARTORPSQQLRSL-NGEWRLMRYFLLTHLCGISHRIWCTLSTICS-DAA. In one embodiment, $\Psi$ can be arg-gly.

The invention also features an expression vehicle comprising DNA encoding the above-described protein, and regulatory DNA positioned and oriented to effect its expression. For example, the protein-encoding DNA comprises a nucleotide sequence of about 1011 base pairs identical to, or encoding the same amino acids as, the first 1011 base pairs of the *E. coli* pheA structural gene. Also preferably, the regulatory DNA comprises a promoter (e.g., lacP) that is not subject to phenylalanine feedback regulation and specifically lacks any attenuator sequence intervening between the promoter and the protein-encoding DNA. Moreover, the promoter may control expression of an artificial operon that includes the protein-encoding DNA and DNA encoding a phenylalanine synthesis pathway enzyme other than CMPD, e.g., DNA encoding DAHP synthase.

Microbial cells transformed with the expression vehicle are cultured in a fermentation broth from which phenylalanine is recovered.

Finally, the invention features a method of engineering a cell to produce feedback insensitive CMPD, by isolating DNA comprising the *E. coli* pheA gene and converting the codon corresponding to the TGG codon for tryptophan 338 into a TGA stop codon.

We have recognized that the catalytically critical segment of *E. coli* CMPD lies within its N-terminal 337 amino acids, that phenylalanine feedback sensitivity depends on a single amino acid, tryptophan 338, and that deletion of the entire 49 C-terminal amino acids of CMPD does not destroy catalytic activity but does substantially destroy feedback sensitivity. Similarly, substitution of other amino acid(s) for trp 338 results in a feedback insensitive enzyme. The resulting CMPD-active, phenylalanine-insensitive enzymes are useful, particularly for in vivo phenylalanine synthesis, because the penultimate two synthesis steps (chorismate→prephenate→phenylpyruvate) proceed even in the presence of phenylalanine product, thus enabling greater product yields, all other things being equal.

Other features and advantages of the invention will be apparent from the following description of the preferred embodiments thereof, and from the claims.

DESCRIPTION OF THE PREFERRED EMBODIMENTS

First, the drawings will be described briefly.

DRAWINGS

ABBREVIATIONS

The following three-letter and single-letter codes are used for amino acids:

Ala, A—alanine
Arg, R—arginine
Asn, N—asparagine
Asp, D—aspartic acid
Cys, C—cysteine
Gln, Q—glutamine
Glu, E—glutamic aicd
Gly, G—glycine
His, H—histidine
Ile, I—isoleucine
Leu, L—leucine
Lys, K—lysine
Met, M—methionine
Phe, F—phenylalanine
Pro, P—proline
Ser, S—serine
Thr, T—threonine
Trp, W—tryptophan
Tyr, Y—tyrosine
Val, V—valine

GENETIC STRUCTURES

Figure 1:
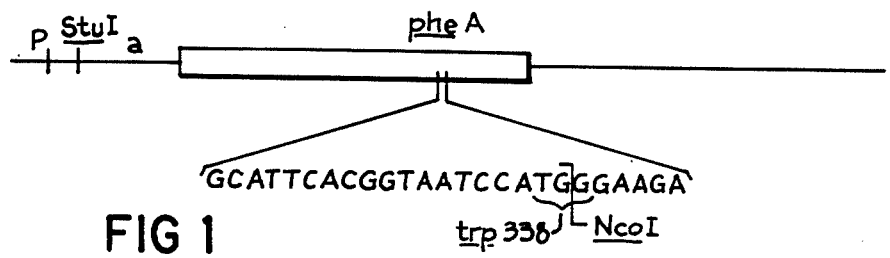
FIG. 1 is a diagrammatic representation of selected restriction enzyme cleavage sites in an *E. coli* chromosomal segment that includes the pheA gene and surrounding regions.

Referring to FIG. 1, the horizontal line represents the chromosomal DNA of *E. coli* encoding chorismate-mutase-prephenate dehydratase (pheA) and its surrounding regions. The box represents the translated region of pheA. The tryptophan amino acid residue at position 338, 49 amino acids away from the carboxy terminus of the protein, is shown, and NcoI represents a restriction endonuclease cleavage site, the sequence of which contains the codon for the tryptophan residue. "P" represents the promoter of pheA, and "A" a transcription attenuator within the 5' end of the pheA control region. The nucleotide and amino acid sequences of pheA and CMPD given in Hudson and Davidson (1984) are incorporated by reference.

The expression vector can be assembled from readily available components using techniques such as those described in Maniatis et al., *Molecular Cloning, A Laboratory Manual*, Cold Spring Harbor 1982. For example, the pheA gene can be derived from pKB45 [Zurawski et al. *Proc. Nat'l. Acad. Sci.* 75: 4271–4274 (1978)], or from other plasmids such as pKB663 (deposited in *E. coli* YMC9, ATCC 39462, and described in co-pending commonly owned U.S. application, Backman Ser. No. 653,193, filed Sept. 24, 1984, which is hereby incorporated by reference). The pheA gene (FIG. 1) can be truncated or altered as generally described below to yield pheA',.a gene coding for phenylalanine-insensitive CMPD. The pheA' gene is then spliced to a suitable promoter and other regulatory DNA. For example, the pheA' is spliced to lacP, derived from pKB663 (referenced above), or from pKB430 (referenced below).

The novel operon can be constructed as generally described in Ser. No. 653,193, referenced above, using a gene encoding another phenylalanine synthesis pathway enzyme, e.g. aroF. For example, aroF can be derived from pKB45, referenced above, or from appropriate digests of pKB712 (ATCC 39856) or pKB750 (ATCC 39857) each of which is described in the above-referenced Ser. No. 653,193.

Specifically, a truncated pheA gene (termed pheA') which determines an active CMPD enzyme lacking the C-terminal 49 amino acids can be constructed by deleting the DNA from the NcoI site in the pheA gene (FIG. 1) through the end of the gene. This altered gene has a stop codon (TGA) in place of a naturally-occuring tryptophan codon (TGG). This deletion can be prepared repeatably from any cloned pheA gene by NcoI cleavage, filling in the resulting sticky ends with DNA polymerase, and abutting to a DNA end beginning with an A (e.g., a filled-in EcoRI end).

Determination that the resulting altered enzyme is feedback resistant is accomplished by assay of either chorismate mutase or prephenate dehydratase (using the technique of Gething et al. (1976) *Eur. J. Biochem.* 71: 317-325) in the presence of sufficient phenylalanine to feedback inhibit wild type CMPD. Neither activity of the truncated CMPD is affected by phenylalanine at concentrations of at least of 1.2 mM. Moreover, the CMPD activity and phenylalanine insensitivity are retained when the truncated CMPD is expressed as a fusion with other peptides or proteins, e.g., the lacZ alpha peptide. Finally, the CMPD activity and phenylalanine insensitivity are retained when an amino acid substitution to wild-type CMPD is made at trp 338.

The following examples are illustrative, and are not intended to limit the invention.

EXAMPLE 1

(pheA', pKB631)

Figure 2:
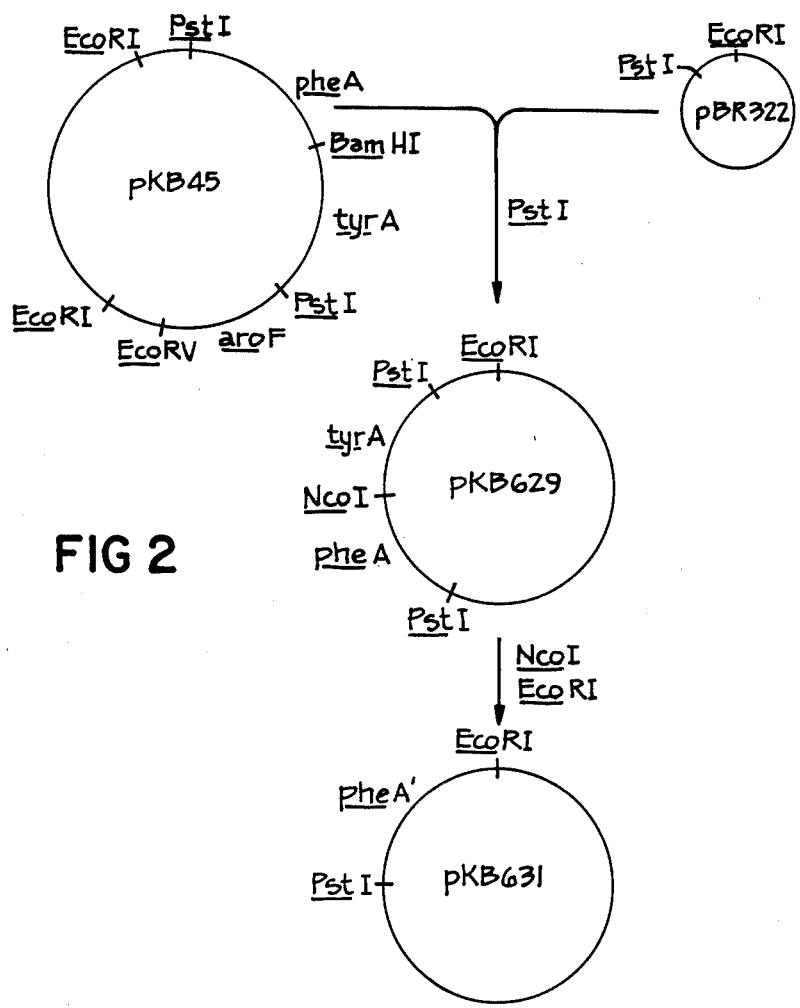
FIG. 2 is a diagrammatic representation of construction of a truncated pheA termed pheA'.

Referring to FIG. 2, pKB45 (referenced above) was cleaved with PstI and ligated into PstI cut pBR322 (ATCC 37017) to give pKB629. This plasmid was then cleaved with NcoI and EcoRI; the sticky ends were filled in with DNA polymerase and ligated together, to give pKB631. pKB631 contains the 5' portion of pheA in a truncated form which we have termed pheA'.

EXAMPLE 2

(lacP-pheA', pKB823)

Figure 3:
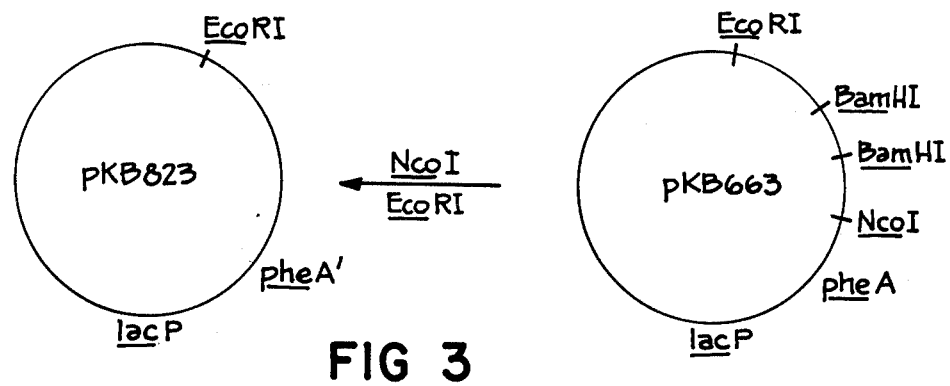
FIG. 3 is a diagrammatic representation of the construction of a lacP pheA' fusion.

Referring to FIG. 3, a pheA' derivative of pKB663 (deposited in *E. coli* ATCC strain 39462) was constructed by deleting the NcoI-EcoRI fragment of pKB663 and religating the plasmid together to yield pKB823, in which the pheA' gene is under the control of the lac promoter. As explained below, this construction includes a weak attenuator sequence between lacP and pheA'.

EXAMPLES 3 AND 4

(pheA'-aroF fusions pKB684 and pKB689)

Figure 5:
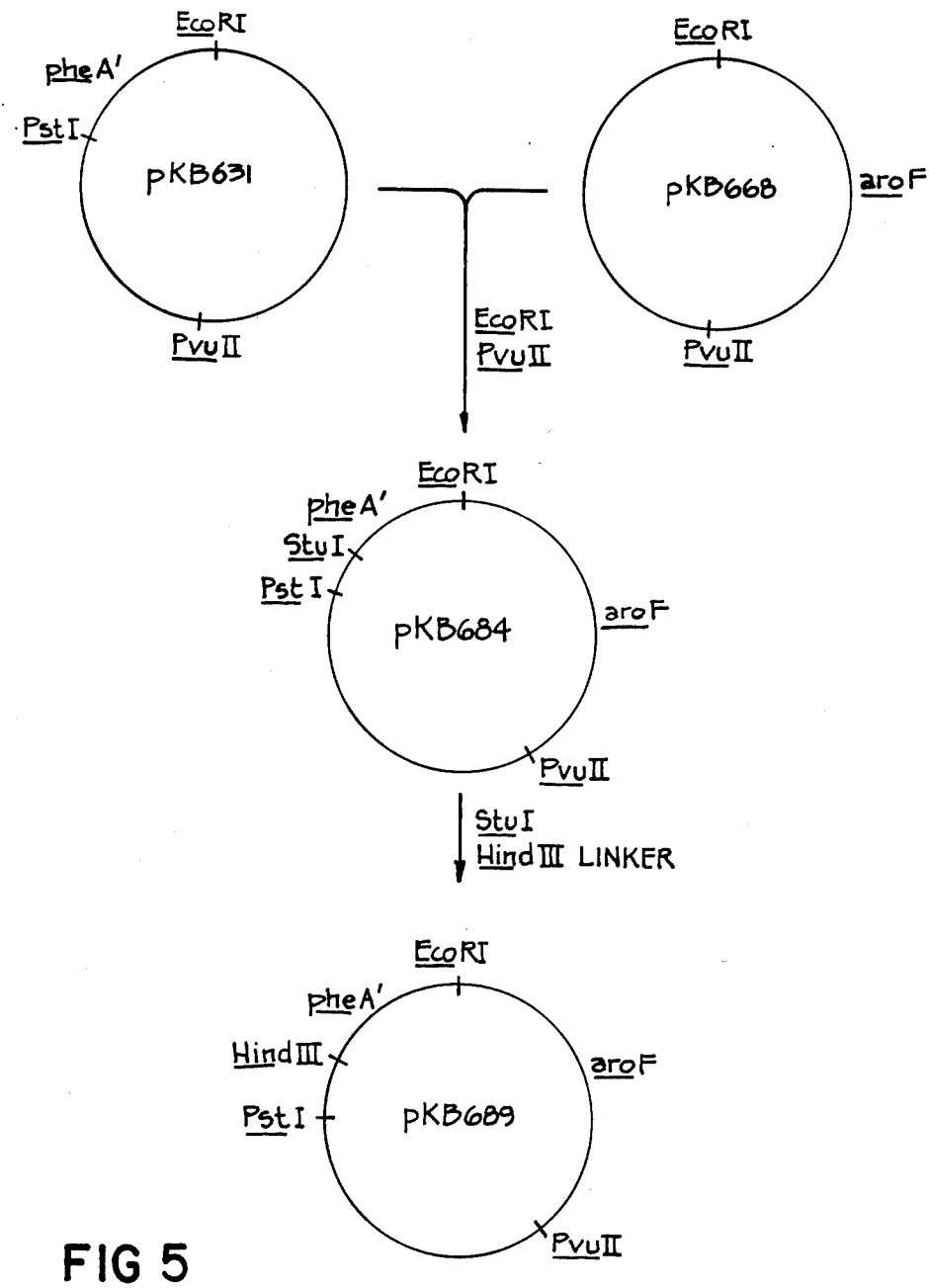
FIG. 5 is a diagrammatic representation of the construction of a pheA' aroF fusion.

Referring to FIG. 5, pKB631 (FIG. 2) was used to fuse pheA' to aroF by cleaving both pKB631 and pKB668 (Ser. No. 653,193, cited above) with EcoRI and Pvu II and ligating the appropriate fragments together, yielding pKB684. In this construction, the pheA' gene would be transcribed from the pheA promoter. The StuI site on pKB684 is then converted to a Hind III site by cutting with StuI and ligating Hind III linkers into the site, yielding pKB689. This process places a linker between the promoter and operon of pheA, so that a heterologous promoter can be readily inserted if desired.

EXAMPLES 5, 6, AND 7

(pheA'-aroF fusion, lacP, pKB694, pKB697, pKB702)

Figure 4:
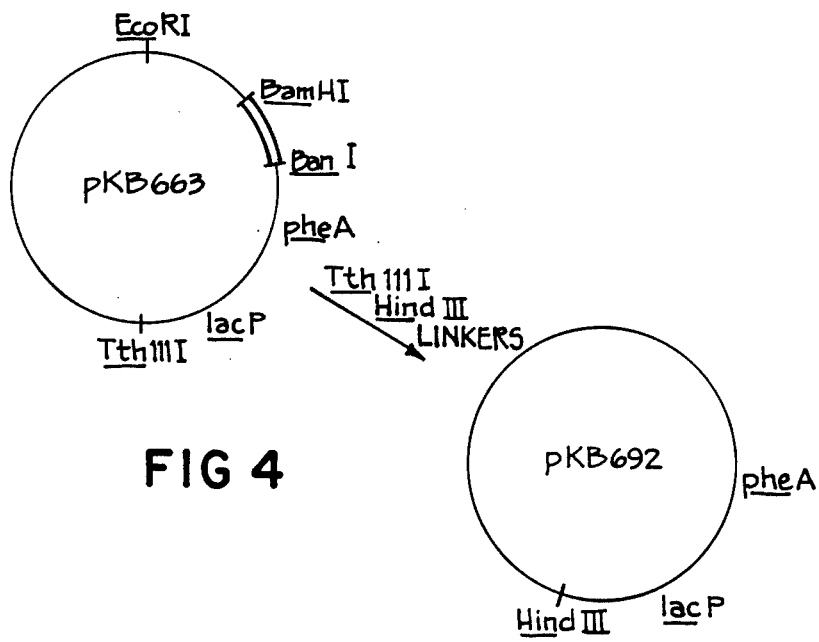
FIG. 4 is a diagrammatic representation of the construction of pKB692.
Figure 6:
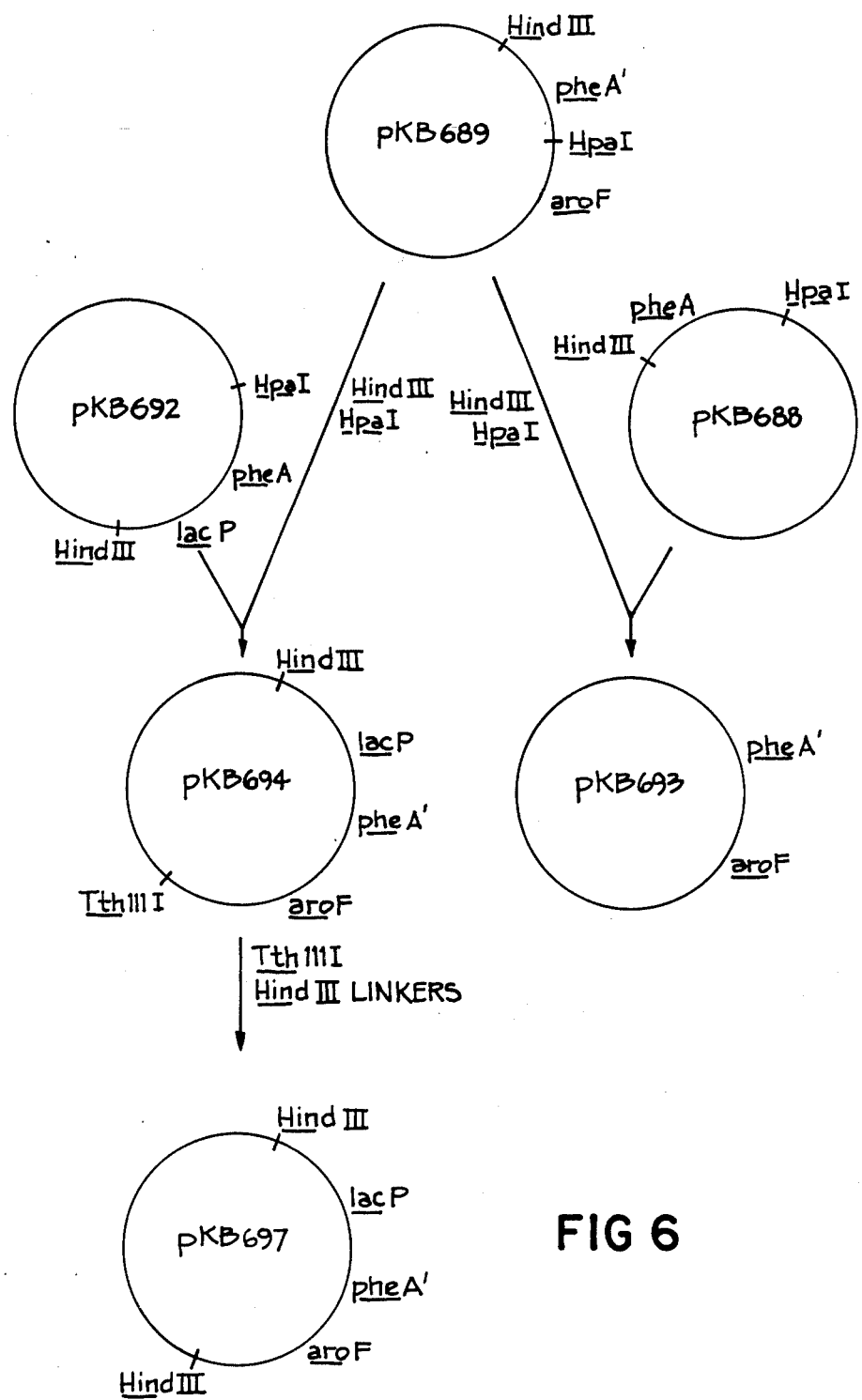
FIGS. 6 and 7 are diagrammatic representations of the construction of pKB697 and pKB693.
Figure 8:
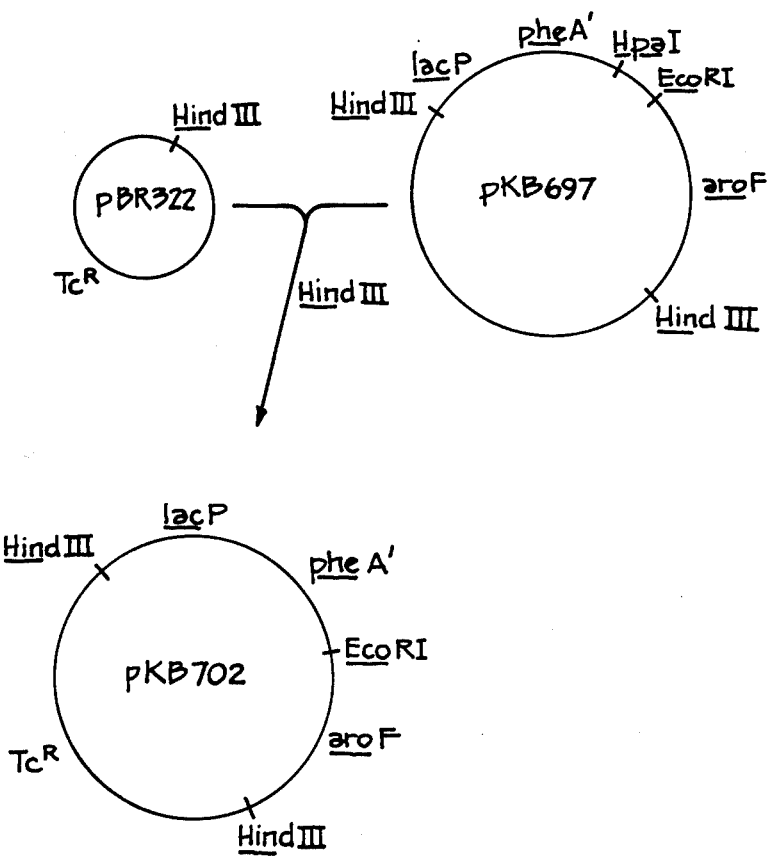
FIG. 8 is a diagrammatic representation of the construction of pKB702.

As shown in FIG. 4, the TthlllI site in pKB663 (referenced above) near the lacP DNA was converted to a more convenient Hind III site using Hind III linkers, to give pKB692. Plasmid pKB694 was then constructed by treating pKB689 (FIG. 6) and pKB692 (FIG. 4) with Hind III and Hpa I, and ligating the relevant fragments, as shown in FIG. 6. This plasmid is a varient of the pheA'-aroF operon of Examples 3, and 4, except that the pheA promoter has been supplemented by the lac promoter. The TthlllI site on pKB694 was converted to a Hind III site using Hind III linkers, yielding pKB697 (FIG. 6). This was done so that a plasmid which determines tetracycline resistance could be derived from pKB697 as shown in FIG. 8, by fusing Hind III cut pBR322 with Hind III cut pKB697 to yield pKB702 (deposited in ATCC strain 67068). This resistance factor facilitates manipulation and selection of the plasmid.

EXAMPLE 8

(pheA'-aroF fusion lacking attenuator, pKB693)

Wild-type pheA includes an attenuator sequence that operates to regulate transcription in the presence of sufficient phenylalanine to form a leader peptide. It has been found that in some previous pheA-aroF fusions, expressed from a foreign promoter such as the lac promoter, at least some of this attenuator sequence remains between the promoter and the pheA or pheA' gene and appears to exert some regulatory effect on transcription, thus reducing the level of pheA or pheA' expression. It is desirable to eliminate the attenuator sequence entirely. Specifically, pKB693, which lacks the attenuator sequence, is derived from pKB689, which includes at least some of the attenuator sequence, (FIG. 5) as shown in FIGS. 6 and 7 and as described below.

Figure 7:
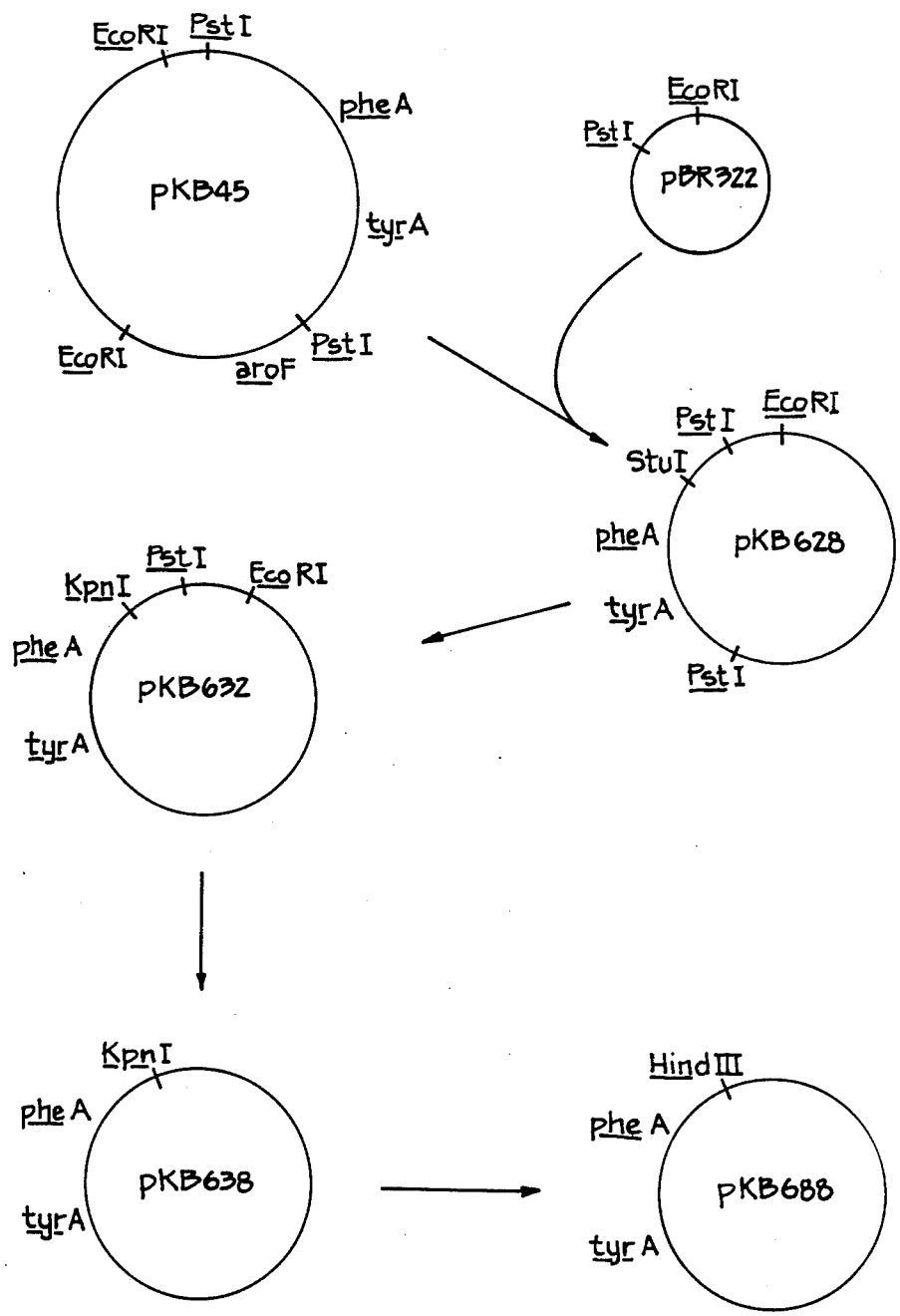

In FIG. 7, pKB45 and pBR322 (referenced above) are ligated with Pst I and recircularized yielding pKB628. pKB628 is cleaved at Stu I, chewed back with an exonuclease and resealed with a Kpn I linker, yielding pKB632. pKB632 is cleaved at Kpn I, chewed back further with an exonuclease, and resealed with a Kpn I linker, yielding pKB638. The Kpn I site in pKB638 is converted to a Hind III site by a linker, yielding pKB688.

In FIG. 6, pKB693 is constructed by treating pKB689 (FIG. 5) and pKB688 (FIG. 7) with Hind III and Hpa I and ligating fragments (selected by size separation on agarose gels) together.

EXAMPLE 9 lacP-pheA' lacking attenuator (pKB912)

Figure 9:
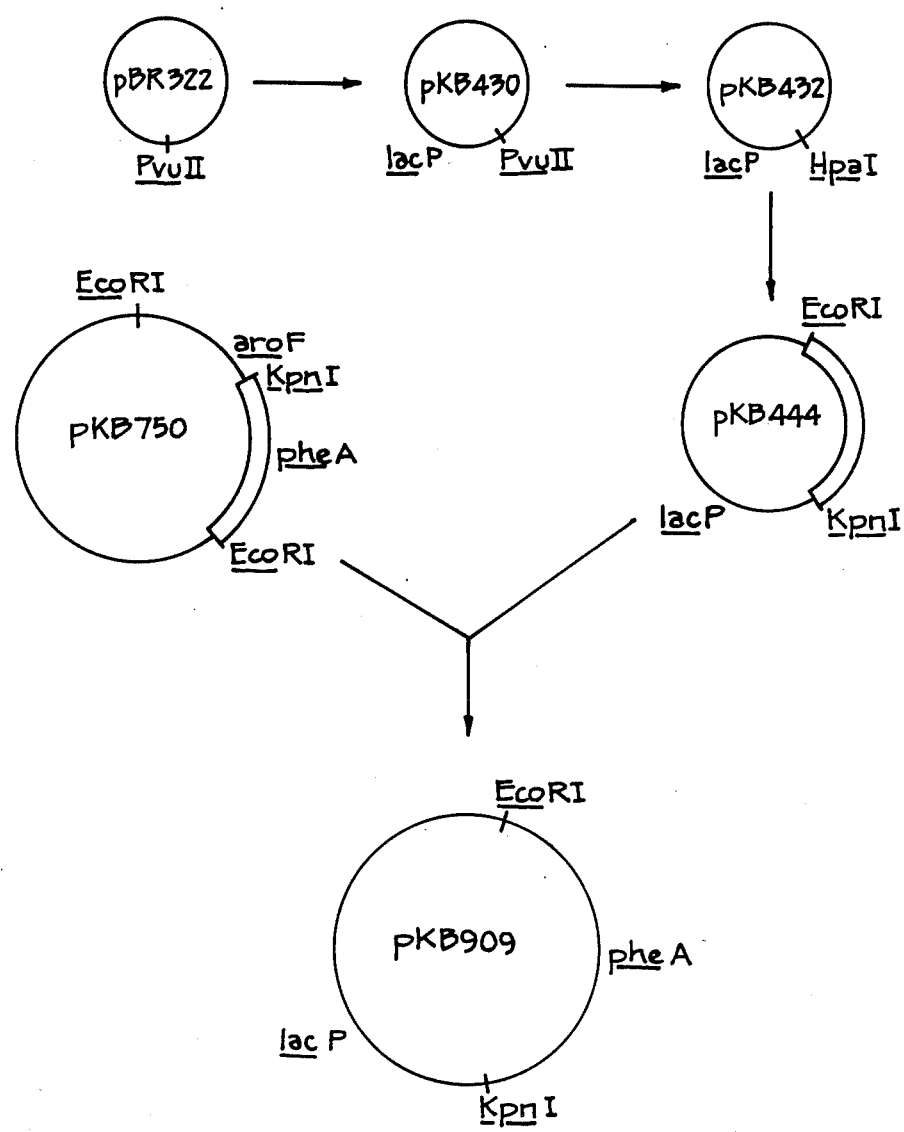
FIGS. 9 and 10 are diagrammatic representations of the construction of plasmids containing a lacP-pheA' fusions.
Figure 10:
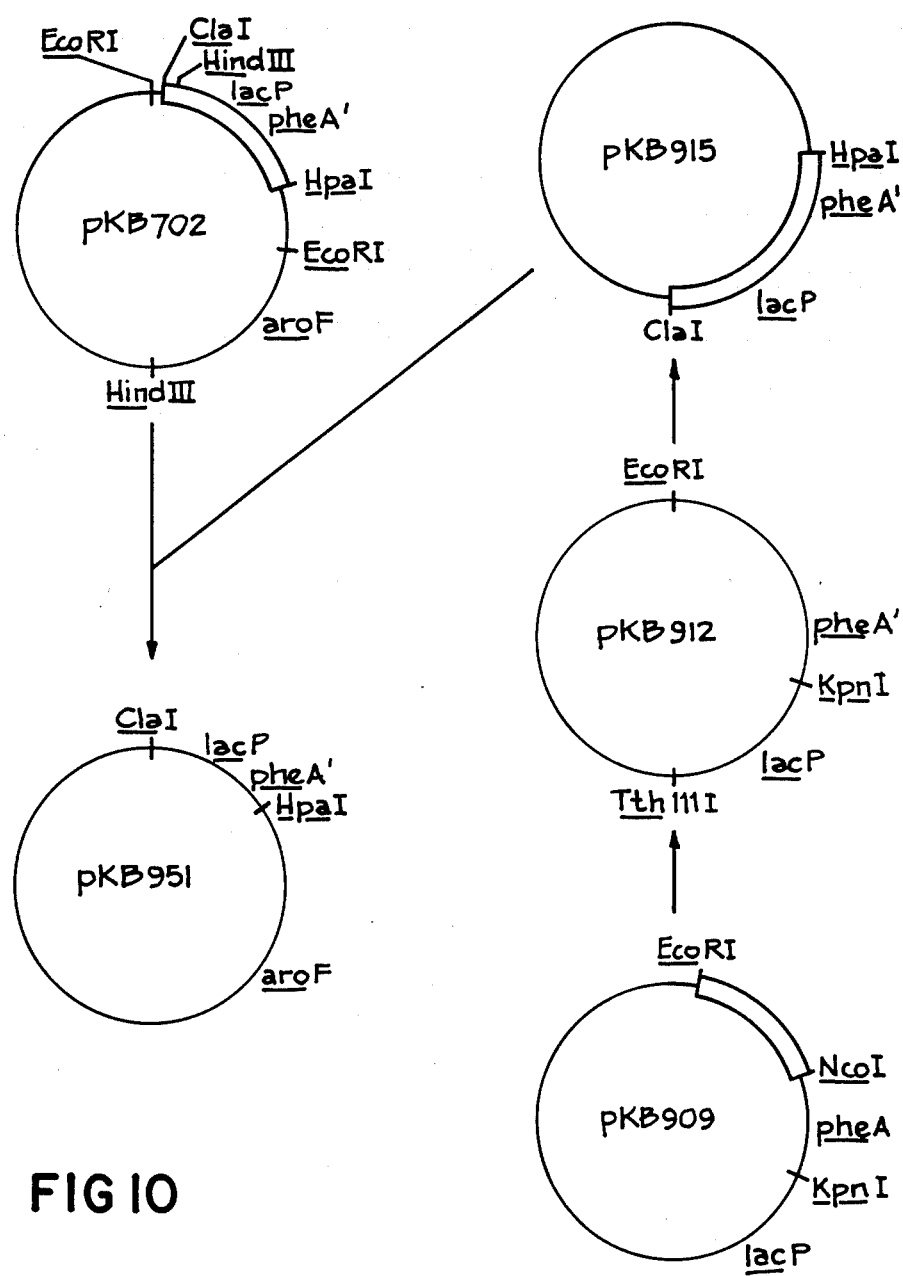

Another pheA' construction lacking the above-described attenuator DNA is pKB912 (deposited in ATCC 67067), constructed as shown in FIGS. 9 and 10. In FIG. 9, the Kpn I-EcoRI fragment of pKB750 (ATCC 39857, referenced in Ser. No. 653,193) includes the pheA gene without the attenuator DNA. That fragment is cloned onto pKB444 to yield pKB909. Then, as shown in FIG. 10, the Nco I-EcoRI fragment from pKB909 is deleted, yielding the lacP-pheA' fusion of pKB912, which is deposited in ATCC 67067. As shown in FIG. 9, pKB444 is derived from pKB430 (a pBR322 derivative described in Ser. No. 653,193) by changing the Pvu II site of pKB430 first to Hpa I and then to Kpn I using linkers.

EXAMPLE 10 lacP-pheA'-aroF lacking attenuator (pKB951)

A plasmid carrying the new lacP-pheA' fusion and also carrying aroF is constructed. This plasmid, pKB951 (FIG. 10), is an analogue of pKB712 (Ser. No. 653,193), which has been previously used for biosynthesis of phenylalanine. pKB951 is constructed from pKB912 by converting the TthlllI site to a ClaI site, using ClaI linkers, removing the ClaI-HpaI fragment and ligating it to the appropriate ClaI-HpaI fragment of pKB702 (FIG. 8).

EXAMPLE 11

Substitution for trp 338 of pheA (pKB894)

A small change in pheA (resulting in replacement of the tryptophan 338 residue in the wild type enzyme by an arginine-glycine dipeptide) substantially removes sensitivity to feedback inhibition.

Figure 11:
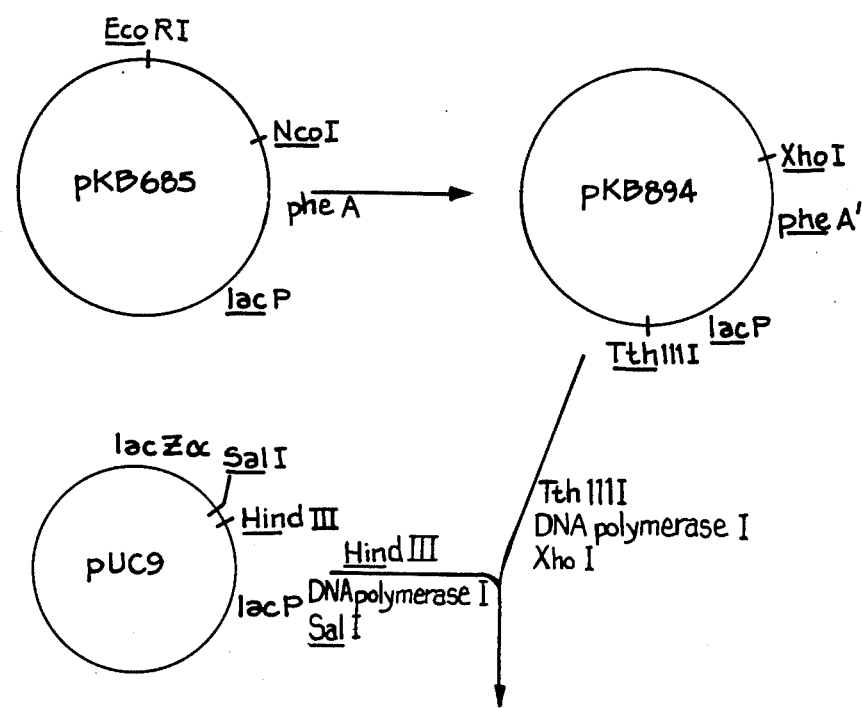
FIG. 11 is a schematic representation of the construction of a pheA'-lacZ fusion and of an in-frame substitution in the pheA gene.
Figure 11:
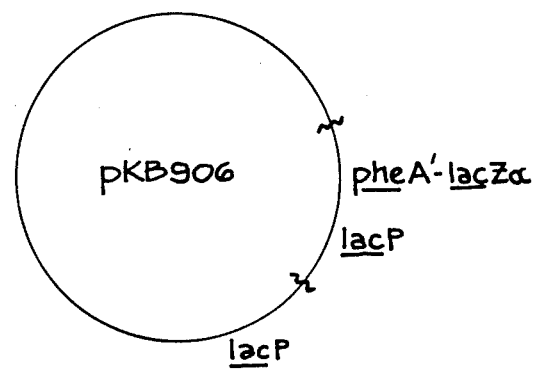

The above noted alteration is made by cleavage of pheA with NcoI, treatment of the linearized DNA with mung bean nuclease, and reclosure of the DNA with addition of an XhoI linker, as shown in FIG. 11, in the conversion of pKB685 (derived from pKB663 by deletion of the BanI-BamHI fragment shown in FIG. 3) to pKB894. Although this procedure is not ordinarily expected to cause the specific change referred to above, sequence analysis showed that an extra nucleotide was serendipitously removed (most likely by the mung bean nuclease treatment), yielding the observed result. One skilled in the art will recognize that there are other ways to obtain this construction, for example, by synthesizing an appropriate DNA fragment.

EXAMPLE 15 pheA'-lacZ fusions pheA' is fused to a portion of the lacZ gene, yielding a pheA'-lacZ alpha peptide fusion (FIG. 11). The resulting fusion retains CMPD activity. The fusion is formed by cloning a lacP-pheA' gene fragment from pKB894 to the lacZ gene in pUC9, which is commercially available and is referenced in Yanisch et al., cited above. The lacZ portion of the fusion has the sequence: RRIPGN-SLAVVLQRRDWENPGVTQLNRLAAHP-PFASWRNSEEARTORPSQQLRSLNGEWRL-MRYFLLTHLCGISHRIWCTLSTICSDAA.

pKB894 is cut with TthlllI, rendered blunt with DNA polymerase I and cut with XhoI. pUC9 is cut with Hind III, rendered blunt with DNA polymerase I and cut with SalI. The XhoI and SalI ends are joined as are the blunt ends, to yield pKB906.

Plasmids pKB912 and pKB702 in *E. coli* K12 strain MM294 have been deposited in the ATCC and assigned numbers 67067 and 67068 respectively. Applicants' assignees, BioTechnica International, and H. J. Heinz Company acknowledge their responsibility to replace these cultures should they die before the end of the term of a patent issued hereon, 5 years after the last request for a culture, or 30 years, whichever is the longer, and their responsibility to notify the depository of the issuance of such a patent, at which time the deposits will be made available to the public. Until that time the deposits will be made available to the Commissioner of Patents under the terms of 37 CFR Section 1—and 35 USC Section 112.

PHENYLALANINE PRODUCTION

In order to produce phenylalanine, one of the above-described expression vectors is transformed by standard techniques into an appropriate microorganism so that the phenylalanine insensitive CMPD is produced in the microorganism. The vectors of the invention generally enable increased phenylalanine production in host organisms. Those skilled in the art will be able to select appropriate microorganisms and, if necessary, to make appropriate modifications to the vectors to adapt them to particular hosts. *E. coli* is generally a suitable organism particularly for the above-described specific vectors pKB702 and pKB912. Those skilled in the art will recognize that other desirable traits may be incorporated into the host organism by engineering to enhance production of the desired product.

The transformed organisms are cultured in a suitable medium, and phenylalanine is recovered. Those skilled in the art of growing bacterial cells will appreciate that a wide range of growth media will be suitable for practicing the invention, including media recipes disclosed in Miller, *Experiments in Molecular Genetics*, Cold Spring Harbor 1972, and the following recipe for minimal salts medium:

(15 g/l glucose, 0.3 g/l MgSO$_4$.7H$_2$O,
14.7 mg/l Cacl$_2$.2H$_2$O,
0.5 g/l NaCl,
5 g/l (NH$_4$)$_2$SO$_4$,
5 mg/l Vitamin B$_1$,
1.5 g/l KH$_2$PO$_4$,
7.5 mg/l FeSO$_4$.7H$_2$O,
1 g/l Na citrate, and 10 ml of micronutrient solution per liter broth.

Micronutrient solution has the following composition:
0.015 g/l Na$_2$MoO$_4$.2H$_2$O,
0.25 g/l H$_3$BO$_3$,
0.07 g/l CoCl$_2$.6H$_2$O,
0.025 g/l CuSO$_4$.5H$_2$O,
0.16 g/l MnCl$_2$.4H$_2$O, and
0.03 g/l ZnSO$_4$.7H$_2$O).

OTHER EMBODIMENTS

Those skilled in the art will recognize that other sequences having CMPD can be engineered. For example, starting with a pheA' sequence such as appears in pKB702 or pKB912, standard engineering techniques can be used to derive other sequences, e.g., by truncating and substituting for residues in the pheA' sequence, and testing the resulting engineered sequence for CMPD activity. Such modified pheA' sequences may be greater or less than 337 residues, and they are included within the claims. For example, the *E. coli* pheA-encoded sequence, altered only by deletion of trp 338, should retain CMPD activity and substantially lack phenylalanine feedback sensitivity. Other expression vectors having regulatory DNA can be used, and other expression systems can be used.

We claim:

1. A protein comprising the following sequence:

MTSENPLLALREKISALDEKLLALLAERRELAVEVGKA

KLLSHRPVRDIDRERDLLERLITLGKAHHLDAHYITRL

FQLIIEDSVLTQQALLQQHLNKINPHSARIAFLGPKGS

YSHLAARQYAARHFEQFIESGCAKFADIFNQVETGQAD

YAVVPIENTSSGAINDVYDLLQHTSLSIVGEMTLTIDH

CLLVSGTTDLSTINTVYSHPQPFQQCSKFLNRYPHWKI

EYTESTSAAMEKVAQAKSPHVAALGSEAGGTLYGLQVL

ERIEANQRQNFTRFVVLARKAINVSDQVPAKTTLLMAT

GQQAGALVEALLVLRNHNLIMTRLESRPIHGNPX, where X is an amino acid residue selected from the group consisting of A, R, N, D, C, Q, E, G, H, I, L, K, M, F, P, S, T, V and Y.

2. The protein of claim 1 wherein the C-terminus of said sequence is attached to a phenylalanine synthesis pathway enzyme.

3. The protein of claim 1 wherein X is R, and the C-terminus of said sequence is attached to a G residue.

4. The protein of claim 1 wherein the C-terminus of said sequence is attached to the lacZα peptide encoded by portion of pUC19.

5. The protein of claim 1 wherein X is E and the C-terminus of said sequence is attached to the following sequence:

EMFYLDIQANLESAEMQKALKEL-
GEITRSMKVLGCYPSENVVPVDPT.

6. A protein having the following C-terminal sequence:

MTSENPLLALREKISALDEKLLALLAERRELAVEVGKAKL
LSHRPVRDIDRERDLLERLITLGKAHHLDAHYITRLFQLI
IEDSVLTQQALLQQHLNKINPHSARIAFLGPKGSYSHLAA
RQYAARHFEQFIESGCAKFADIFNQVETGQADYAVVPIEN
TSSGAINDVYDLLQHTSLSIVGEMTLTIDHCLLVSGTTDL
STINTVYSHPQPFQQCSKFLNRYPHWKIEYTESTSAAMEK
VAQAKSPHVAALGSEAGGTLYGLQVLERIEANQRQNFTRF
VVLARKAINVSDQVPAKTTLLMATGQQAGALVEALLVLRN
HNLIMTRLESRPIHGNP.

7. The protein of claim 1 or claim 6 wherein the N-terminal residue of said sequence is the N-terminal residue of said protein.

* * * * *

UNITED STATES PATENT AND TRADEMARK OFFICE
CERTIFICATE OF CORRECTION

PATENT NO. : 4,753,883
DATED : June 28, 1988
INVENTOR(S) : Keith C. Backman et al.

It is certified that error appears in the above-identified patent and that said Letters Patent are hereby corrected as shown below:

ON THE TITLE PAGE:

Under Assignee: H.J. Heinz Company
Pittsburgh, Pennsylvania should also be listed in addition to BioTechnica International, Inc.

Column 7, line 1, "Example 15" should be --Example 12--.

Column 7, line 30, "Section 1-and" should be --Section 1-14 and--.

Column 8, line 19, "having regulatory" should be --having other regulatory--.

Signed and Sealed this

Thirty-first Day of January, 1989

*Attest:*

DONALD J. QUIGG

*Attesting Officer*      *Commissioner of Patents and Trademarks*